US00PP17217P2

(12) United States Plant Patent
Jonkers

(10) Patent No.: US PP17,217 P2
(45) Date of Patent: Nov. 14, 2006

(54) ***DIASCIA* PLANT NAMED 'DALA DESAL'**

(50) Latin Name: *Diascia barberae*
Varietal Denomination: Dala Desal

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/269,333

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP16,236 P2 * 2/2006 Schrader ..... Plt./263

OTHER PUBLICATIONS

UPOV ROM GTITM Computer Database, GTI Jouve Retrieval Software 2005/05 Citations for 'Dala Desal'.*

* cited by examiner

*Primary Examiner*—Wendy Haas
(74) *Attorney, Agent, or Firm*—Jondle & Associates P.C.

(57) ABSTRACT

A new *Diascia* plant particularly distinguished by large salmon-orange flowers, medium-green foliage with large rounded leaves, vigorous growth, and a round and tall plant habit is disclosed.

1 Drawing Sheet

Genus and species: *Diascia barberae.*
Variety denomination: 'Dala Desal'.

BACKGROUND OF THE NEW PLANT

The present invention comprises a new and distinct cultivar of *Diascia*, botanically known as *Diascia barberae*, and hereinafter referred to by the cultivar name 'Dala Desal'. The new cultivar originated from a hybridization made in 2003 in Andijk, The Netherlands. The female parent is a proprietary *Diascia* plant designated 'DSZ-39-5' (unpatented), having a deep rose flower color and the male parent is a proprietary *Diascia* plant designated 'DSZ-41-3' (unpatented), having a lilac-rose flower color. The seeds produced by the hybridization were sown in May 2003, and the resulting seedlings were selected in July 2003. A single plant selection was chosen for further evaluation and for asexual propagation in the fall of 2003.

The new cultivar was created in 2003 in Andijk, The Netherlands and has been asexually reproduced repeatedly by vegetative cuttings and tissue culture micropropagation in Andijk, The Netherlands over a two-year period. The plant has also been trialed at Gilroy, Calif. The present invention has been found to retain its distinctive characteristics through successive asexual propagations.

Plant Breeder's Rights for this cultivar were applied for in Europe on Jan. 24, 2005 and in Canada on Mar. 31, 2005.

SUMMARY OF THE INVENTION

The following are the most outstanding and distinguishing characteristics of this new cultivar when grown under normal horticultural practices in Gilroy, Calif. and Andijk, The Netherlands.

1. Large salmon-orange-colored flowers;
2. Medium-green foliage with relatively large rounded leaves;

3. A vigorous growth habit; and
4. A round and relatively tall plant habit.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three 6-month-old plants grown in a greenhouse with natural light in a spring trial setting.

The accompanying photograph shows blooms, buds, mature foliage, and plant habit; the inset shows mature inflorescences and buds.

DESCRIPTION OF THE NEW CULTIVAR

The following detailed descriptions set forth the distinctive characteristics of 'Dala Desal'. The data which define these characteristics were collected from asexual reproductions carried out in Hillscheid, Germany. The plant history was taken on seven-month-old plants grown, 3 plants each, in 35-cm-diameter baskets (capable of holding 5-liters of soil) in an outdoor trial field under poly-cover rain protection. Color readings were taken under natural light. Color references are primarily to The R.H.S. Colour Chart of The Royal Horticultural Society of London (R.H.S.) (2001 edition). Texture description details were observed under a magnifying glass.

DESCRIPTION OF THE NEW PLANT

Classification:
*Family.*—Scrophulariaceae.
*Botanical name.*—*Diascia barberae* Hook.
Parentage:
*Female parent.*—'DSZ-39-5' a proprietary deep rose-colored *Diascia* plant (unpatented).

*Male parent.*—'DSZ-41-3' a proprietary lilac rose-colored *Diascia* plant (unpatented).

Growth:

*Form and growth habit.*—Bushy, rounded, semi-upright and semi-trailing.

*Height.*—33 cm (from top of soil) for 7-month-old plants to 45 cm (total vertical height) of a plant in a hanging basket.

*Width.*—70 cm.

*Spread* (*including flowers*).—65 cm, from the base of the main stem to the tips of the branches.

*Time to produce a finished flowering plant.*—About 10 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—About 20 days.

*Root description.*—Fibrous and freely branching.

Leaves:

*Arrangement.*—Single and opposite.

*Shape.*—Deltoid to cordate.

*Apex.*—Obtuse.

*Base.*—Weakly cordate.

*Margin.*—Weakly serrate.

*Immature.*—Color: Upper surface: Between RHS 137D and RHS 143A. Lower surface: RHS 138B. Texture: Very finely pubescent.

*Mature* (*fully expanded*).—Length: 2.1–2.5 cm. Width: 1.9–2.1 cm. Color: Upper surface: RHS 137A to RHS 137B. Lower surface: RHS 138B.

*Venation.*—Type: Pinnate. Color: RHS 144B.

*Texture.*—Appears smooth and glabrous.

*Petiole.*—Length: 0.3 cm. Width: 0.2 cm. Color: RHS 144A.

Stems:

*Length.*—40 to 50 cm without the inflorescence.

*Diameter.*—0.3–0.4 cm as measured in the middle (is square not round).

*Internode length.*—3.0–4.0 cm.

*Color.*—RHS 143B (grass-green).

*Texture.*—Appears smooth and glabrous, but has sparse pubescence.

*Anthocyanin.*—Absent.

Flower bud:

*Shape.*—Round and flattened.

*Diameter.*—0.7 cm.

*Length.*—0.4 cm.

*Color* (*at tight bud*).—RHS 38D and RHS 39B at the base.

Inflorescence:

*Inflorescence type.*—Terminal raceme with flowers in an alternate arrangement at a distance of 0.5 to 1.0 cm.

*Blooming habit.*—Continuous.

*Quantity of inflorescences per plant.*—100.

*Lastingness of individual blooms on the plant.*—3–4 days.

*Fragrance.*—None.

*Inflorescence length.*—10–11 cm.

*Penduncle.*—Color: RHS 143A. Length: 10.5 Diameter: About 0.2 cm. Texture: Finely pubescent.

Flower:

*Type.*—Single, zygomorphic; 5-lobes fused at the base.

*Quantity* (*per raceme*).—3–5 open flowers at the same time; about 20 flowers and buds at various stages of development.

*Shape.*—Salver-shaped.

*Length.*—2.2–2.5 cm.

*Depth.*—0.5 cm.

*Width.*—2.0 cm.

*Color.*—Upper surface: RHS 41C. Lower surface: RHS 43D. Corolla (inside color): RHS 43C; upper petals have a patch of RHS 12A (yellow) at the base.

*Petals* (*lobes*).—Quantity: 5. Arrangement: Two upper lobes (mainly fused) with two lateral lobes and one lower lobe. Apex: Rounded. Base: Fused. Margin: Entire. Texture: Smooth.

*Upper lobes, size.*—Length (from the Corolla opening): 0.6–0.7 cm. Width: 1.0 cm.

*Lateral lobes, size.*—Length (from the Corolla opening): 0.5–0.6 cm. Width: 0.9 cm. Spur: Shape: Funnel-shaped and directed downwards. Length: 0.7–0.8 cm. Diameter: 0.2–0.3 cm. Color: RHS 41D.

*Lower lobe.*—Length (from the Corolla opening): 1.1 cm. Width: 1.6 cm.

*Sepals.*—Quantity: 5. Color: RHS 143A. Length: 0.2–0.3 cm. Width: 0.1 cm. Shape: Deltoid to lanceolate. Apex: Acute. Base: Fused. Anthocyanin: Absent. Texture: Rough with distinct pubescence.

*Pedicels.*—Color: RHS 144B to RHS 147A. Length: 1.5 cm. Diameter: 0.1 cm. Texture: Finely pubescent.

Reproductive organs:

*Stamens.*—Quantity: 4; coherent, arching towards and somewhat twisting around the pistil. Filament: Color: RHS N77A (dark-purple). Length: 0.3–0.4 cm. Diameter: 0.1 cm. Anther color: RHS 13D (pale yellow). Pollen amount: Abundant. Pollen color: RHS 13A.

*Pistils.*—Quantity: 1. Length: 0.3–0.4 cm. Stigma color: RHS 145A. Style color: RHS 143C.

Fruit and seed set: Has not been observed.

Disease and insect resistance: Has not been observed.

COMPARISON WITH PARENTAL AND COMMERCIAL CULTIVARS

'Dala Desal' differs from the female parent, proprietary *Diascia* plant 'DSZ-39-5' (unpatented), in that 'Dala Desal' has a salmon-orange flower color, while 'DSZ-39-5' has a deep rose flower color. Additionally, 'Dala Desal' has a more vigorous growth habit than 'DSZ-39-5'.

'Dala Desal' differs from the male parent, proprietary *Diascia* plant 'DSZ-41-3' (unpatented), in that 'Dala Desal' has a salmon -orange flower color, while 'DSZ-41-3' has a lilac-rose flower color. Additionally, 'Dala Desal' has a more vigorous growth habit, and has a more upright or spreading and less prostrate or trailing plant habit than 'DSZ-41-3'.

'Dala Desal' differs from the commercial cultivar 'Flying Colors Upright Apricot' (unpatented) in that 'Dala Desal' has a more reddish, less salmon-orange flower color, deeper green foliage, and rounder-shaped leaves than 'Flying Colors Upright Apricot'.

'Dala Desal' differs from the commercial cultivar 'Flying Colors Salmon' (unpatented) in that 'Dala Desal' is earlier to flower and has larger flowers of a deeper salmon hue than 'Flying Colors Salmon'.

I claim:

1. A new and distinct cultivar of *Diascia* plant as shown and described herein.

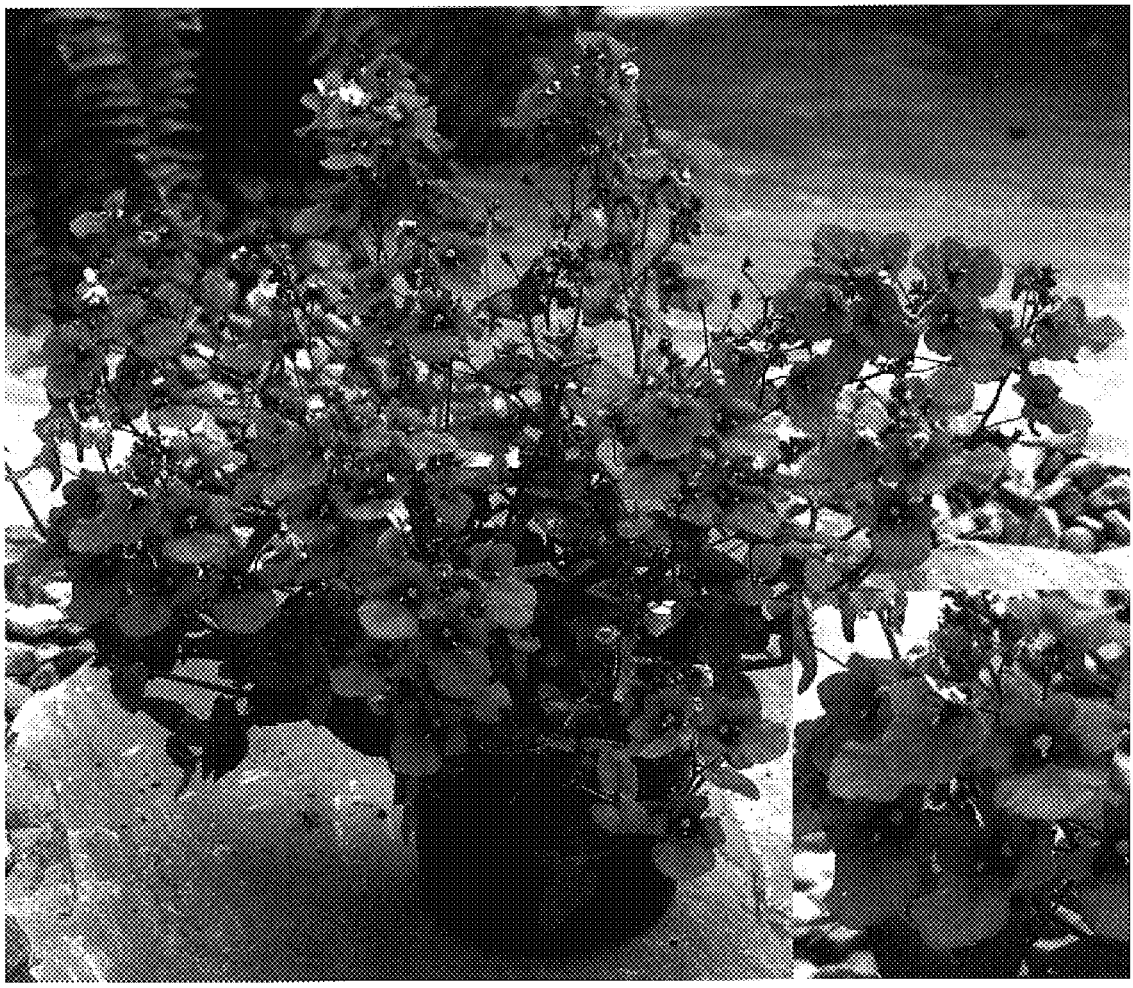

* * * * *